United States Patent
Tylenda et al.

(10) Patent No.: US 9,195,803 B2
(45) Date of Patent: Nov. 24, 2015

(54) SYSTEMS, METHODS, APPARATUSES, AND COMPUTER PROGRAM PRODUCTS FOR PROVIDING CONTROLLED ACCESS TO INTRAVENOUS BAGS

(71) Applicant: Aesynt Incorporated, Cranberry, PA (US)

(72) Inventors: Ben H. Tylenda, Venetia, PA (US); Paul J. Santmyer, Canonsburg, PA (US); D. Scott Souerwine, Freedom, PA (US)

(73) Assignee: Aesynt Incorporated, Cranberry, PA (US)

( * ) Notice: Subject to any disclaimer, the term of this patent is extended or adjusted under 35 U.S.C. 154(b) by 207 days.

(21) Appl. No.: 13/852,320

(22) Filed: Mar. 28, 2013

(65) Prior Publication Data

US 2014/0297027 A1    Oct. 2, 2014

(51) Int. Cl.
  *G06F 17/00*  (2006.01)
  *G06F 19/00*  (2011.01)
  *G07F 17/00*  (2006.01)

(52) U.S. Cl.
  CPC .......... *G06F 19/3456* (2013.01); *G06F 19/327* (2013.01); *G06F 19/3462* (2013.01); *G07F 17/0092* (2013.01)

(58) Field of Classification Search
  CPC .................. G07F 17/0092; A47B 88/0485
  See application file for complete search history.

(56) References Cited

U.S. PATENT DOCUMENTS

| | | |
|---|---|---|
| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,314,243 A | 5/1994 | McDonald et al. |
| 5,346,297 A | 9/1994 | Colson, Jr. et al. |
| 5,377,864 A | 1/1995 | Blechl et al. |
| 5,405,048 A | 4/1995 | Rogers et al. |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |

(Continued)

FOREIGN PATENT DOCUMENTS

WO    WO-2010/114918 A1    10/2010

*Primary Examiner* — Timothy Waggoner (74) *Attorney, Agent, or Firm* — Alston & Bird LLP (57) ABSTRACT

A system, method, apparatus, and computer program product are provided for controlling access to intravenous bags. A system may include a cabinet including a vertically oriented drawer configured to be movable between an open position and a closed position relative to the cabinet, where the contents of the vertically oriented drawer are configured to be accessible from two opposing sides of the vertically oriented drawer when the drawer is in the open position. Systems of example embodiments may include a plurality of overpacks configured to be received within the vertically oriented drawer of the cabinet, where each of the plurality of overpacks is configured to receive therein a single intravenous bag, where each of the plurality of overpacks may include a retention feature, and where the retention feature of each overpack may be configured to be received by a complementary retention feature in the vertically oriented drawer.

18 Claims, 6 Drawing Sheets

(56) References Cited

U.S. PATENT DOCUMENTS

| | | | |
|---|---|---|---|
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |
| 5,745,366 A | 4/1998 | Higham et al. | |
| 5,761,877 A | 6/1998 | Quandt | |
| 5,797,515 A | 8/1998 | Liff et al. | |
| 5,805,456 A | 9/1998 | Higham et al. | |
| 5,842,976 A | 12/1998 | Williamson | |
| 5,878,885 A | 3/1999 | Wangu et al. | |
| 5,880,443 A | 3/1999 | McDonald et al. | |
| 5,883,806 A | 3/1999 | Meador et al. | |
| 5,893,697 A | 4/1999 | Zini et al. | |
| 5,905,653 A * | 5/1999 | Higham et al. | 700/244 |
| 5,912,818 A | 6/1999 | McGrady et al. | |
| 5,927,540 A | 7/1999 | Godlewski | |
| 5,940,306 A | 8/1999 | Gardner et al. | |
| 5,971,593 A | 10/1999 | McGrady | |
| 6,003,006 A | 12/1999 | Colella et al. | |
| 6,011,999 A | 1/2000 | Holmes | |
| 6,021,392 A | 2/2000 | Lester et al. | |
| 6,039,467 A | 3/2000 | Holmes | |
| 6,065,819 A | 5/2000 | Holmes et al. | |
| 6,068,156 A | 5/2000 | Liff et al. | |
| 6,109,774 A | 8/2000 | Holmes et al. | |
| 6,112,502 A | 9/2000 | Frederick et al. | |
| 6,116,461 A | 9/2000 | Broadfield et al. | |
| 6,151,536 A | 11/2000 | Arnold et al. | |
| 6,170,230 B1 | 1/2001 | Chudy et al. | |
| 6,176,392 B1 | 1/2001 | William et al. | |
| 6,189,727 B1 | 2/2001 | Shoenfeld | |
| 6,223,934 B1 | 5/2001 | Shoenfeld | |
| 6,231,138 B1 * | 5/2001 | Janson | 312/201 |
| 6,256,967 B1 | 7/2001 | Hebron et al. | |
| 6,283,322 B1 | 9/2001 | Liff et al. | |
| 6,289,656 B1 | 9/2001 | Wangu et al. | |
| 6,338,007 B1 | 1/2002 | Broadfield et al. | |
| 6,339,732 B1 | 1/2002 | Phoon et al. | |
| 6,361,263 B1 | 3/2002 | Dewey et al. | |
| 6,370,841 B1 | 4/2002 | Chudy et al. | |
| 6,393,339 B1 * | 5/2002 | Yeadon | 700/237 |
| 6,449,927 B2 | 9/2002 | Hebron et al. | |
| 6,471,089 B2 | 10/2002 | Liff et al. | |
| 6,497,342 B2 | 12/2002 | Zhang et al. | |
| 6,499,270 B2 | 12/2002 | Peroni et al. | |
| 6,532,399 B2 | 3/2003 | Mase | |
| 6,564,121 B1 | 5/2003 | Wallace et al. | |
| 6,581,798 B2 | 6/2003 | Liff et al. | |
| 6,609,047 B1 | 8/2003 | Lipps | |
| 6,611,733 B1 | 8/2003 | De La Huerga | |
| 6,625,952 B1 | 9/2003 | Chudy et al. | |
| 6,640,159 B2 | 10/2003 | Holmes et al. | |
| 6,650,964 B2 | 11/2003 | Spano, Jr. et al. | |
| 6,671,579 B2 | 12/2003 | Spano, Jr. et al. | |
| 6,681,149 B2 | 1/2004 | William et al. | |
| 6,742,671 B2 | 6/2004 | Hebron et al. | |
| 6,755,931 B2 | 6/2004 | Vollm et al. | |
| 6,760,643 B2 | 7/2004 | Lipps | |
| 6,776,304 B2 | 8/2004 | Liff et al. | |
| 6,785,589 B2 | 8/2004 | Eggenberger et al. | |
| 6,790,198 B1 | 9/2004 | White et al. | |
| 6,814,254 B2 | 11/2004 | Liff et al. | |
| 6,814,255 B2 | 11/2004 | Liff et al. | |
| 6,847,861 B2 | 1/2005 | Lunak et al. | |
| 6,874,684 B1 | 4/2005 | Denenberg et al. | |
| 6,892,780 B2 | 5/2005 | Vollm et al. | |
| 6,895,304 B2 | 5/2005 | Spano, Jr. et al. | |
| 6,975,922 B2 | 12/2005 | Duncan et al. | |
| 6,985,797 B2 | 1/2006 | Spano, Jr. et al. | |
| 6,996,455 B2 | 2/2006 | Eggenberger et al. | |
| 7,010,389 B2 | 3/2006 | Lunak et al. | |
| 7,014,063 B2 | 3/2006 | Shows et al. | |
| 7,016,766 B2 | 3/2006 | William et al. | |
| 7,040,504 B2 | 5/2006 | Broadfield et al. | |
| 7,052,097 B2 | 5/2006 | Meek, Jr. et al. | |
| 7,072,737 B2 | 7/2006 | Lunak et al. | |
| 7,072,855 B1 | 7/2006 | Godlewski et al. | |
| 7,077,286 B2 | 7/2006 | Shows et al. | |
| 7,085,621 B2 | 8/2006 | Spano, Jr. et al. | |
| 7,092,796 B2 | 8/2006 | Vanderveen | |
| 7,093,755 B2 | 8/2006 | Jordan et al. | |
| 7,100,792 B2 | 9/2006 | Hunter et al. | |
| 7,103,419 B2 | 9/2006 | Engleson et al. | |
| 7,111,780 B2 | 9/2006 | Broussard et al. | |
| 7,139,639 B2 | 11/2006 | Broussard et al. | |
| 7,142,944 B2 * | 11/2006 | Holmes et al. | 700/237 |
| 7,150,724 B2 | 12/2006 | Morris et al. | |
| 7,171,277 B2 | 1/2007 | Engleson et al. | |
| 7,194,333 B2 * | 3/2007 | Shoenfeld | 700/243 |
| 7,218,231 B2 | 5/2007 | Higham | |
| 7,228,198 B2 | 6/2007 | Vollm et al. | |
| 7,249,688 B2 | 7/2007 | Hunter et al. | |
| 7,348,884 B2 | 3/2008 | Higham | |
| 7,417,729 B2 | 8/2008 | Greenwald | |
| 7,419,133 B2 | 9/2008 | Clarke et al. | |
| 7,426,425 B2 | 9/2008 | Meek, Jr. et al. | |
| 7,554,449 B2 | 6/2009 | Higham | |
| 7,571,024 B2 | 8/2009 | Duncan et al. | |
| 7,588,167 B2 | 9/2009 | Hunter et al. | |
| 7,887,146 B1 * | 2/2011 | Louie et al. | 312/209 |
| 8,094,028 B2 * | 1/2012 | Braun et al. | 340/572.8 |
| 8,831,770 B2 * | 9/2014 | Heffron | 700/214 |

* cited by examiner

SYSTEMS, METHODS, APPARATUSES, AND COMPUTER PROGRAM PRODUCTS FOR PROVIDING CONTROLLED ACCESS TO INTRAVENOUS BAGS

TECHNOLOGICAL FIELD

Embodiments of the present invention relate generally to storing, tracking, controlling access to, and dispensing items and, more particularly, to systems, methods, apparatuses, and computer program products for providing controlled access to intravenous bags.

BACKGROUND

In many instances, access to objects may be controlled, such as for purposes of monitoring inventory, preventing unauthorized access to the objects, and/or the like. For example, in the case of valuable and/or controlled objects or items, such as medical items, it may be important to track access to those objects to reduce the chance that an unauthorized party has accessed an object and/or to facilitate inventory tracking. Accordingly, efforts are ongoing to develop improved systems to provide controlled access to objects, such as products to be dispensed.

BRIEF SUMMARY OF SOME EXAMPLES OF THE INVENTION

Systems, methods, apparatuses, and computer program products are herein provided for controlling access to intravenous bags. Systems, methods, and apparatuses in accordance with various embodiments provide several advantages to conventional methods of managing intravenous bag inventory and/or controlling access thereto. In this regard, some example embodiments provide a system for controlling access to intravenous bags. More particularly, some embodiments use a cabinet configured with vertically oriented, individually lockable drawers in conjunction with an inventory control system to control access to the contents of the vertically oriented drawers and to keep track of inventory within the cabinet.

An example embodiment of the present invention may provide a system for controlling access to intravenous bags. The system may include a cabinet including a vertically oriented drawer configured to be movable between an open position and a closed position relative to the cabinet, where the contents of the vertically oriented drawer are configured to be accessible from two opposing sides of the vertically oriented drawer when the drawer is in the open position. Systems of example embodiments may include a plurality of overpacks configured to be received within the vertically oriented drawer of the cabinet, where each of the plurality of overpacks is configured to receive therein a single intravenous bag, where each of the plurality of overpacks may include a retention feature, and where the retention feature of each overpack may be configured to be received by a complementary retention feature in the vertically oriented drawer.

According to some embodiments of the present invention, each overpack contained within the vertically oriented drawer may be accessible from a first side of the drawer and an opposing second side of the drawer, where each of the plurality of overpacks may be configured to be opened from both the first side of the drawer and the second side of the drawer. The retention feature of each overpack may include a hook and the retention feature of the drawer may include a rod. The vertically oriented rawer may be individually lockable. Embodiments may include a visual indicator for the drawer to indicate if the drawer is unlocked. The system may be configured to detect that the contents of an overpack of the plurality of overpacks have been removed. Each overpack may include a sensor configured to sense the presence of an intravenous bag within the overpack. The system may be configured to receive a signal from the sensor to determine if the corresponding overpack includes an intravenous bag. Each of the plurality of overpacks may include a unique identifier, and an intravenous bag received within a respective overpack may be associated with the unique identifier.

Embodiments of the present invention may provide a method for controlling access to intravenous bags. Methods may include receiving an intravenous bag into an overpack, associating an identifier of the intravenous bag with an identifier of the overpack, receiving the overpack in a vertically oriented drawer, securing the vertically oriented drawer in a closed position, receiving a request for the intravenous bag, and providing for access to the overpack in response to receiving the request for the intravenous bag. Providing for access to the overpack may include causing the vertically oriented drawer containing the overpack to be unlocked. Receiving a request for the intravenous bag may include receiving a request for the intravenous bag and verifying that the request is from an authorized medical person. Methods may include storing in a memory the identity and the location of the intravenous bag within the vertically oriented drawer. Methods may optionally include providing for an indication of the location of the intravenous bag in response to receiving a request for the intravenous bag. Providing for an indication of the location of the intravenous bag may include providing a visual indicator of the vertically oriented drawer in which the intravenous bag is located. Methods may include receiving an indication that the contents of the overpack have been accessed. Methods may still further include updating an inventory of the vertically oriented drawer in response to receiving an indication that the contents of the overpack have been accessed.

According to another example embodiment of the invention, a system for controlling access to intravenous bags may be provided. The system may include one or more vertically oriented drawers, a plurality of overpacks received within the one or more vertically oriented drawers, where each of the plurality of overpacks is configured to receive therein an intravenous bag, and where each of the plurality of overpacks includes an identification. Systems according to some embodiments may optionally include an inventory management system configured to receive an indication of the identification of an overpack of the plurality of overpacks and an identification of the intravenous bag received therein. The inventory management system may further be configured to receive an indication of access to an overpack of the plurality of overpacks and to update an inventory of the system in response to receiving the indication. The inventory management system may further be configured to receive a request for an intravenous bag, where the inventory management system is configured to provide access to an overpack of the plurality of overpacks containing the requested intravenous bag. The inventory management system may further be configured to provide a visual indicator of a location of the overpack containing the requested intravenous bag in response to receiving the request for the intravenous bag.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information" and similar terms may be used interchangeably to refer to data capable of being transmitted, received, displayed and/or stored in accordance with various example embodiments. Thus, use of any such terms should not be taken to limit the spirit and scope of the disclosure. Further, where a computing device is described herein to receive data from or send data to another computing device, it will be appreciated that the data may be received directly from or sent directly to another computing device, or may be received/sent indirectly via one or more intermediary computing devices, such as, for example, one or more servers, relays, routers, network access points, and/or the like.

Embodiments of the present invention may be used for storage and distribution, and control of access to articles, such as intravenous bags within a healthcare facility. Embodiments may be implemented in any environment in which it is desirable to store, monitor access, control access, and/or dispense articles from a storage location. However, embodiments of the present invention are herein described with respect to healthcare facilities, such as hospitals, physicians' offices, healthcare clinics, and any other facility that manages and/or stores intravenous bags.

Embodiments of the present invention may be used to monitor access to drawers and the contents therein which may be accessed through opening of the drawer and accessing an overpack therein containing the intravenous bag that is sought. As intravenous bags are in substantially non-structured packaging (i.e., flexible bags), they tend to be difficult to handle, and may be difficult to store efficiently. Accordingly, intravenous bags for which access is to be controlled according to embodiments of the present invention may be received within overpacks. Overpacks, or packaging that encases or holds the intravenous bags, may be more structured than the intravenous bag and may provide a more uniform form factor for the handling and storage of intravenous bags, as described further below.

Figure 1:
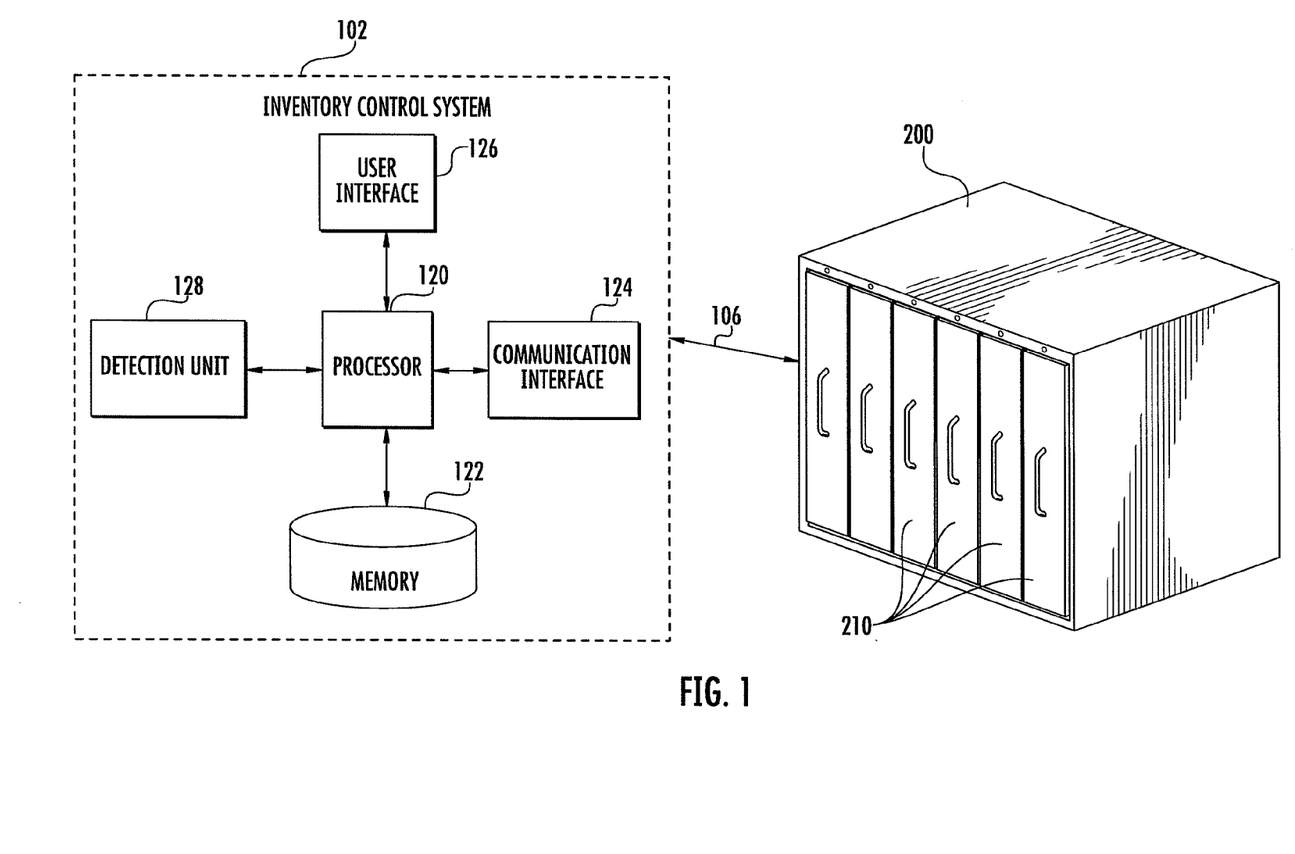
FIG. 1 illustrates a system for controlling access to articles including intravenous bags according to an example embodiment of the present invention.

FIG. 1 illustrates a system for controlling access to intravenous bags according to some example embodiments. It will be appreciated that the system, as well as the illustrations in other figures, are each provided as an example of some embodiments and should not be construed to narrow the scope or spirit of the disclosure in any way. In this regard, the scope of the disclosure encompasses many potential embodiments in addition to those illustrated and described herein. As such, while FIG. 1 illustrates one example of a configuration of a system for controlling access to intravenous bags, numerous other configurations may also be used to implement embodiments of the present invention.

The illustrated embodiment includes a cabinet 200 including a plurality of vertically oriented drawers 210. The drawers may each hold therein a plurality of intravenous bags which may be received within overpacks as outlined below. The cabinet 200 may be configured to be in communication with an inventory control system 102 which controls access to the drawers 210 and monitors inventory levels within the cabinet 200.

The inventory control system 102 may include any computing device or plurality of computing devices configured to interface with a cabinet 200 via a communications link 106. By way of non-limiting example, the inventory control system 102 may comprise a desktop computer, laptop computer, tablet computer, mobile computing device, server, embedded computing device, and/or the like. FIG. 1 illustrates a block diagram of the inventory control system 102 of an example embodiment which includes various means for performing the various functions described herein. These means may include, for example, one or more of a processor 120, memory 122, communication interface 124, user interface 126, or detection unit 128 for performing the various functions described herein. The means of the system 102 as described herein may be embodied as, for example, circuitry, hardware elements (e.g., a suitably programmed processor, combinational logic circuit, and/or the like), a computer program product comprising a computer-readable medium (e.g., memory 122) storing computer-readable program instructions (e.g., software or firmware) that are executable by a suitably configured processing device (e.g., the processor 120), or some combination thereof.

The processor 120 may, for example, be embodied as various means including one or more microprocessors, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 1 as a single processor, in some embodiments the processor 120 may comprise a plurality of processors. The plurality of processors may be embodied on a single computing device or may be distributed across a plurality of computing devices collectively configured to function as the inventory control system 102. The plurality of processors may be in operative communication with each other and may be collectively configured to perform one or more functionalities of the inventory control system 102 as described herein. In some embodiments, the processor 120 may be configured to execute instructions stored in the memory 122 or otherwise accessible to the processor 120. These instructions, when executed by the processor 120, may cause the inventory control system 102 to perform one or more of the functionalities of the system 102 as described herein. As such, whether configured by hardware or software methods, or by a combination thereof, the processor 120 may comprise an entity capable of performing operations according to embodiments of the present invention while configured accordingly. Thus, for example, when the processor 120 is embodied as an ASIC, FPGA or the like, the processor 120 may comprise specifically configured hardware for conducting one or more operations described herein. Alternatively, as another example, when the processor 120 is embodied as an executor of instructions, such as may be stored in the memory 122, the instructions may specifically configure the processor 120 to perform one or more algorithms and operations described herein.

The memory 122 may include, for example, volatile and/or non-volatile memory. Although illustrated in FIG. 1 as a single memory, the memory 122 may comprise a plurality of memories. The plurality of memories may be embodied on a single computing device or distributed across a plurality of computing devices. The memory 122 may comprise, for example, a hard disk, random access memory, cache memory, flash memory, an optical disc (e.g., a compact disc read only memory (CD-ROM), digital versatile disc read only memory (DVD-ROM), or the like), circuitry configured to store information, or some combination thereof. In this regard, the memory 122 may comprise any non-transitory computer readable storage medium. The memory 122 may be configured to store information, data, applications, instructions, and/or the like for enabling the inventory control system 102 to carry out various functions in accordance with example embodiments of the present invention. For example, in some example embodiments, the memory 122 is configured to buffer input data for processing by the processor 120. Additionally or alternatively, in some example embodiments, the memory 122 is configured to store program instructions for execution by the processor 120. The memory 122 may store information in the form of static and/or dynamic information. This stored information may be stored and/or used by the detection unit 128 during the course of performing its functionalities.

In some example embodiments, the inventory control system 102 may include a communication interface(s), such as the communication interface 124. In embodiments including a communication interface, the communication interface 124 may be embodied as any device or means embodied in circuitry, hardware, a computer program product comprising a computer readable medium (e.g., the memory 122) storing computer readable program instructions executed by a processing device (e.g., the processor 120), or a combination thereof that is configured to receive and/or transmit data from/to another device with which the inventory control system 102 may be in communication. In some example embodiments, the communication interface 124 is at least partially embodied as or otherwise controlled by the processor 120. In this regard, the communication interface 124 may be in communication with the processor 120, such as via a bus. The communication interface 124 may additionally be in communication with the memory 122, user interface 126, and/or detection unit 128, such as via a bus. The communication interface 124 may include, for example, an antenna, a transmitter, a receiver, a transceiver and/or supporting hardware or software for enabling communications with another computing device. The communication interface 124 may be configured to receive and/or transmit data using any protocol that may be used for communications between computing devices. As an example, the communication interface 124 may be configured to be configured receive and/or transmit data from/to the tag reader 104 via the communication link 106.

In some example embodiments, the inventory control system 102 may include a user interface 126. However, in other embodiments, such as some example embodiments in which the inventory control system 102 is embodied as a server or embedded device, some aspects of the user interface 126 may be limited, or the user interface 126 may be omitted altogether. The user interface 126 may be in communication with the processor 120 to receive an indication of a user input and/or to provide an audible, visual, mechanical, or other output to a user. As such, the user interface 126 may include, for example, a keyboard, a mouse, a joystick, a display, a touch screen display, a microphone, a speaker, and/or other input/output mechanisms. The user interface 126 may be in communication with the memory 122, communication interface 124, and/or detection unit 128, such as via a bus.

The detection unit 128 may be embodied as various means, such as circuitry, hardware, a computer program product comprising a computer readable medium (e.g., the memory 122) storing computer readable program instructions executed by a processing device (e.g., the processor 120), or some combination thereof and, in some example embodiments, is embodied as or otherwise controlled by the processor 120. In embodiments wherein the detection unit 128 is embodied separately from the processor 120, the detection unit 128 may be in communication with the processor 120. The detection unit 128 may further be in communication with one or more of the memory 122, communication interface 124, or user interface 126, such as via a bus.

While the inventory control system 102 is illustrated as a unit in FIG. 1, the inventory control system components may be remotely located from the cabinet 200, with a user interface 126 disposed proximate the cabinet 200 to allow an authorized medical person to interface with the inventory control system and access the articles contained within the cabinet. Additionally or alternatively, some or all of the illustrated components of the inventory control system may be located remotely from one another and each may be in communication with other components of the inventory control system by wired or wireless communications.

Cabinets according to example embodiments of the present invention may be located in a fixed, static position within a healthcare facility, such as at a nurse station, central pharmacy, patient room, or healthcare unit (e.g., an intensive care unit), and/or cabinets may be located on a mobile platform. A mobile platform in which cabinets of example embodiments may be implemented may include nurse carts (e.g., a workstation on wheels (WOW) or computer on wheels (COW)), anesthesia carts, automated guided vehicles, etc.

A user may interface with the cabinet via an interface (e.g., user interface 126) that is mounted proximate the cabinet, such as a display and interface mounted to a nurse cart, or a user interface mounted on or near a cabinet in a static location. Additionally or alternatively, a user interface may include a mobile device, such as a portable digital assistant (PDA), cell phone, near-field communication device, etc. from which a user may interact with the cabinet.

Figure 2:
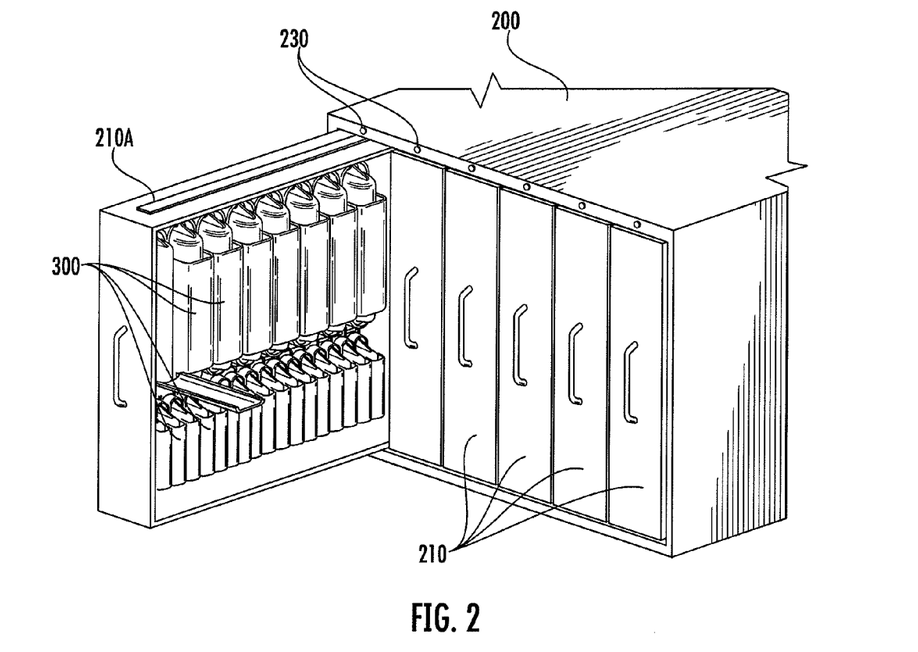
FIG. 2 illustrates a perspective view of a cabinet of a system for controlling access to articles according to an example embodiment of the present invention with a vertically oriented drawer moved to the open position.

FIG. 2 illustrates an example embodiment of a cabinet 200 including vertically oriented drawers 210 with one drawer 210A shown in the open position, wherein the contents (i.e., overpacks 300) are accessible to an authorized medical person. Each drawer 210, 210A may be individually lockable in the closed position (shown as drawers 210) where the contents of the drawers are inaccessible. An inventory control system 102 according to example embodiments may be configured to unlock one or more drawers in response to a request for an article contained within the drawer(s) from an authorized medical person. The drawers may be locked, for example, by electric solenoids which may be actuated by the inventory control system 102 via communications link 106.

In an example embodiment, an authorized medical person, such as a nurse or doctor, may require a particular article, such as an intravenous bag, from the cabinet 200. The authorized medical person may provide this request to the inventory control system 102 via a user interface 126. The user interface 126 may include a mobile device carried by the authorized medical person, a user interface of a mobile nurse cart, or a fixed user interface proximate the cabinet. The request may include a patient name and/or an identification of the article being requested. In advance of or in response to receiving the request, the inventory control system may require identification of the authorized medical person to confirm that the request came from an authorized medical person. Appropriate identification of medical personnel may be important to preclude unauthorized access to medications and to satisfy regulatory requirements. Requiring medical personnel to properly identify themselves may also preclude a nurse from accessing the wrong articles or cabinets by limiting the medical personnel authorized to access a particular cabinet or drawer. Further, requiring identification of medical personnel may provide an audit trail to identify who retrieved medication for a particular patient.

As noted above, embodiments of the present invention may require identification of the authorized medical person before providing access to the medication or supplies dispensed from the cabinet. Identification of authorized medical personnel may be accomplished by the scanning of an identification card which may include a barcode or RFID tag. Alternatively, identification of authorized medical personnel may be accomplished by biometric scanning, such as a scan of a person's retina, finger print, hand geometry, palm vein, face, or voice to determine the identification of the person. Identification may also be provided by a personal identification number (PIN), or any combination of the aforementioned mechanisms.

Upon verifying that a request was received from an authorized medical person, the inventory control system 102 may determine a location of the requested article within a drawer 210, 210A of the cabinet 200, and unlock the drawer containing the requested article. A visual indicator may be provided to indicate to the authorized medical person which drawer contains the requested article. In the illustrated embodiment, a light emitting diode (LED) 230 is arranged above each drawer and the LED may illuminate in a distinct color to indicate that the drawer is unlocked and/or that the drawer contains the article requested. For example, the LED may illuminate red when the drawer is locked and green when the drawer is unlocked. The authorized medical person may then open the appropriate drawer to the open position.

Figure 3:
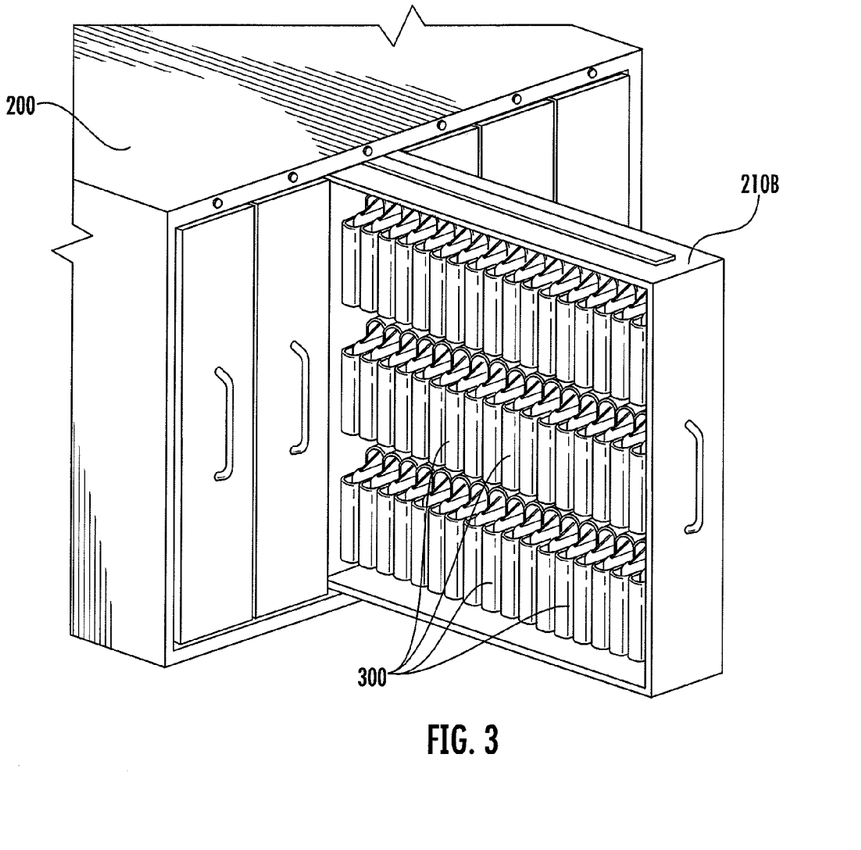
FIG. 3 illustrates another perspective view of the cabinet of FIG. 2 with a vertically oriented drawer moved to the open position.

FIG. 2 illustrates a plurality of overpacks 300 contained within the vertically oriented drawer 210A. The overpacks 300 may each be configured to hold an intravenous bag. FIG. 3 illustrates another view of a cabinet 200 according to example embodiments of the present invention. As illustrated, the vertically oriented drawer 210B may provide access to the contents of the drawer from two opposing sides of the drawer by being open on both sides of the drawer. In practice, the cabinet may be situated against a wall or on a mobile cart where an authorized medical person may be on one side of the cabinet without access to the other side of the cabinet. Regardless of which side of the vertically oriented drawer is accessible to the person, they may still retrieve the requested articles. This feature may be convenient when the cabinet is located in confined areas, such as hallways, patient rooms, etc.

As noted above, the vertically oriented drawers of the illustrated embodiments each include a plurality of overpacks, where the overpacks are configured to contain intravenous bags. Overpacks according to embodiments of the present invention are uniform or quasi-uniform overpacks or secondary packaging for use with a variety of sizes of intravenous bags. Further, while the overpacks may be configured to hold intravenous bags, other articles may also be held within the overpacks either together with an intravenous bag or separately For example, a medication may be concentrated and configured to be mixed into an intravenous bag of saline solution. In such an embodiment, the medication, which may be in a carpuject, syringe, integrated vial, or other form may be transported together with the saline bag, and a single overpack may be used to hold the medication and the saline intravenous bag.

Figure 4:
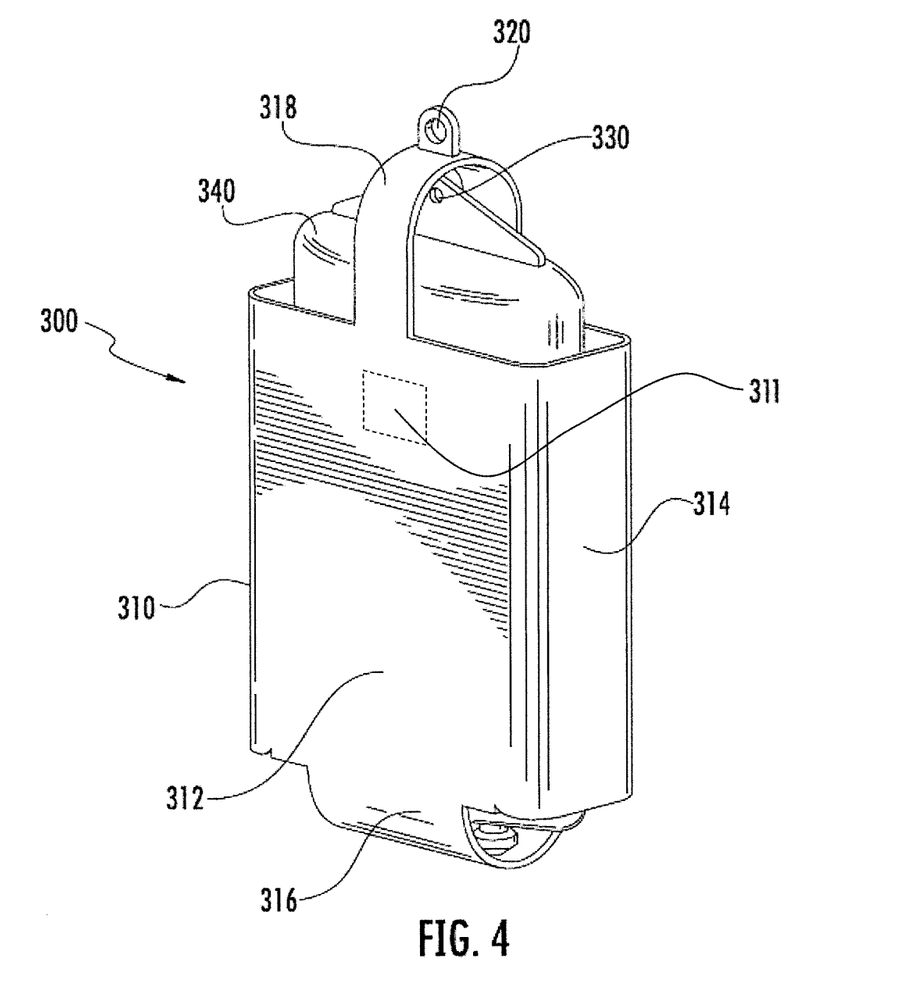
FIG. 4 illustrates an overpack including an intravenous bag therein according to an example embodiment of the present invention.

FIG. 4 illustrates an example embodiment of an overpack 300 according to an example embodiment of the present invention. The illustrated embodiment includes a structured overpack body 310 which is configured to substantially encase the contents. The body 310 provides a front 312, back (not visible), sides 314, and bottom 316. The overpack body 310 further includes a top 318. The overpack 300 of the illustrated embodiment does not fully enclose the intravenous bag 340 contained therein, but provides a structured package to substantially surround the intravenous bag 340. The top 318 of the overpack of the illustrated embodiment includes a retention feature 320. In the illustrated embodiment, the retention feature comprises a loop; however, other example embodiments may include a hook, a carabineer, a snap, a button, or any feature which may allow for removable retention of the overpack within the drawer. The vertically oriented drawer may have a complementary retention feature such as a hook to be received within the loop 320 of the illustrated embodiment or a rod on which overpack hooks may be received.

Overpacks according to example embodiments of the present invention may also be configured with a hook (not shown) disposed under the top 318 configured to engage a hanging loop 330 of an intravenous bag. The hook disposed under the top 318 may support the top of the intravenous bag and suspend at least a portion of the intravenous bag's weight from the hook. In example embodiments where the intravenous bag is not suspended from the top 318 of the overpack, either because the overpack does not include a hook disposed under the top 318 or because the IV bag itself does not include a hanging loop, the bottom 316 may be configured to support the weight of the bag. Additionally, or alternatively, the front 312, back, and sides 314 of the overpack may be further configured support the intravenous bag.

Figure 5:
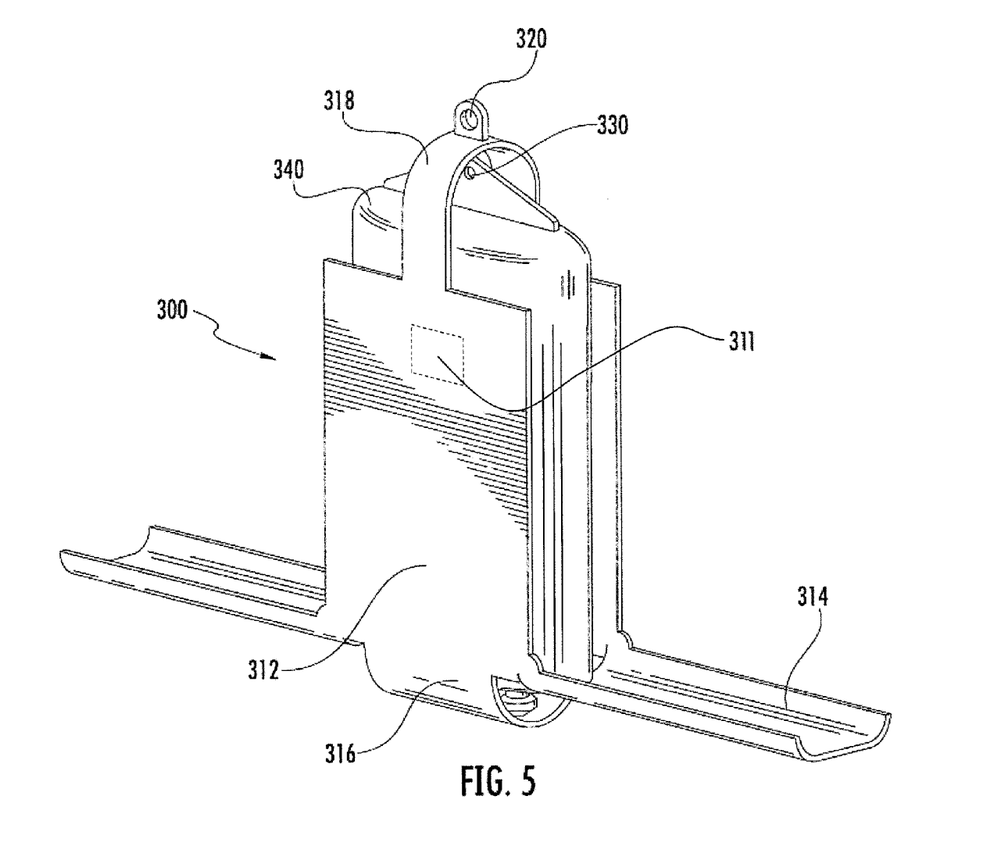
FIG. 5 illustrates the overpack of FIG. 4 in an open position where the contents are accessible.

As shown in FIG. 5, access to the contents of the overpack 300 may be gained through opening one or both of sides 314. The sides 314 may be hinged to allow an authorized medical person to remove the intravenous bag 340 from the overpack 300. As shown, both sides 314 may be openable such that the contents of the overpack may be removed from either side of the vertically oriented drawer without having to remove the overpack 300 from the drawer. In some embodiments, the overpacks may be removable from the vertically oriented drawer. In example embodiments in which the cabinet serves a plurality of patients and an authorized medical person may access the cabinet for a plurality of intravenous bags at once, the overpacks may be removed from the cabinet drawer and the overpacks may be carried by the authorized medical person or temporarily stored on a mobile cart, such as a nurse cart. The authorized medical person may remove the intravenous bags from their overpacks when administering the intravenous bag to the appropriate patient.

The inventory control system of example embodiments may be configured to determine article removal from the cabinet in order to more accurately keep track of inventory. As such, each overpack may be configured such that the inventory control system can detect a removal of the overpack from a drawer, the contents from the overpack (e.g., when the overpack is opened and the IV bag removed), or both.

In an example embodiment of the present invention, an overpack may include a radio frequency identification (RFID), or similar identification, tag and the cabinet may include an RFID, or similar, reader. The RFID tag of each overpack may be unique and may be correlated to the contents of the overpack when the overpack is loaded, for example, at the central pharmacy. Optionally, the overpack and the contents may be correlated when an intravenous bag is loaded to an overpack at the cabinet. A technician may load overpacks by scanning an intravenous bag (e.g., scanning a barcode or RFID tag of the bag with a reader) and scanning the overpack (e.g., scanning a barcode or RFID tag of the overpack) when inserting the intravenous bag into the overpack. The overpack and contents may then be correlated. The correlation between overpack identification and the contents may be stored, for example, in a memory such as the memory 210A of the inventory control system. The memory may be located with the cabinet 200 or may be located remotely, such as accessible via a facility network.

Intravenous bags may be correlated with and loaded into overpacks at the cabinet, or optionally, at a remote location, such as a central pharmacy or offsite distribution facility. The overpacks may be used to aid transport of the intravenous bags through a healthcare facility before being received within a cabinet.

Upon loading an overpack including an intravenous bag into a cabinet, and closing the drawer to the cabinet, the cabinet may be configured to scan the drawer with an RFID reader (e.g., detection unit 128) to determine the overpacks contained therein. The inventory control system 102 may then update the contents of the drawer (e.g., in memory 122) in order to direct an authorized user to a requested intravenous bag. In response to receiving a request from an authorized medical person (e.g., via user interface 126), and verifying the identity of the authorized medical person, the cabinet may indicate which drawer contains the requested intravenous bag, such as by the visual indicator described above. The authorized medical person may then open the drawer and remove the overpack containing the requested intravenous bag. Upon closing the drawer, the cabinet may again use an RFID reader (e.g., detection unit 128) to scan the contents of the drawer and to determine which overpack was removed. The inventory control system may then confirm that the removed overpack correlated to the requested intravenous bag. If the removed overpack does not correlate to the requested intravenous bag, an alert may be issued. The alert may be local to the cabinet (e.g., an audible and/or visual alarm), or broadcast to a nurse station, a mobile device, a nurse cart, etc.

In some example embodiments of the present invention the overpack may not be removed from the drawer when the contents of the overpack are removed by an authorized medical person. In such an embodiment, each overpack may include one or more sensors configured to detect either the presence of an intravenous bag in the overpack, or configured to detect that the overpack has been accessed (e.g., the overpack has been opened). Sensors 311 for detecting the presence of contents may include a proximity sensor, a weight sensor (e.g., strain gauge), a photoelectric sensor, or RFID sensors disposed on opposite sides of an overpack arranged to detect signal interference between the two when an object is received within the overpack. In such an embodiment, in response to a change to the contents in the overpack (i.e., removal or insertion), the sensors 311 may, together with an RFID tag or other near-field communication device, report the change in contents of the overpack to the inventory control system 102. The inventory control system may receive the reported change via the communications interface 124 and update the inventory accordingly.

The aforementioned embodiments refer to an identification tag as RFID tags for purposes of example to describe a radio frequency signal as one type of signal that may be emitted by an identification tag. It will be appreciated, however, that an identification tag may be configured to emit detectable signals other than radio frequency, such as, for example, ultrasound signals, optical signals, electrical current, electrical voltage, an electrical field, a magnetic field, and/or the like. It will thus be appreciated that wherever reference is made to RF tags herein, it is merely one example of a signaling tag and accordingly other types of signaling tags may be substituted for RF tags.

It will be further appreciated that in some example embodiments an identification tag may comprise either an active tag or a passive tag (e.g., an active or passive RF tag). Accordingly, a reader used to monitor a state of a signal emitted by the signaling tag may be configured to passively monitor the signal state or to actively interrogate the signaling tag. As such, any signal emitted by a signaling tag may be emitted in response to being interrogated by a tag reader (e.g., a tag reader of detection unit 128), if the signaling tag is embodied as a passive tag.

The tag reader may be embodied as any identification tag reader configured to read a signal that may be emitted by an identification tag(s) such that a change in state of the signal may be detected by the inventory control system 102. As an example, the tag reader may, for example, comprise an RF tag reader in embodiments in which one or more of the identification tags comprise RF tags. Depending on embodiments of the identification tags, the tag reader may be configured to passively read an emitted signal (e.g., for an active RF tag) and/or to actively interrogate the signaling tag (e.g., for a passive RF tag). The tag reader may be located anywhere within sufficient proximity to detect a change in state of a signal emitted by one or more of the identification tags. The tag reader may, for example, be positioned at a location at which an object to be monitored may be accessed, such as in the cabinet 200.

Although referred to as a tag reader, it will be appreciated that the tag reader may comprise a system including a plurality of components. For example, the tag reader may comprise a tag reader component connected to one or more antennas configured to receive a signal emitted by a signaling tag and transmit the signal to the tag reader component so that the tag reader component may read the signal. As such, the detection unit 128 and communication interface 124 of some example embodiments may be a single unit.

In some embodiments, the communications interface 124 or the detection unit 128 may include a direct wired connection or wireless communications link between the tag reader and inventory control system 102. Additionally or alternatively, in some example embodiments, the communications interface 124 and/or detection unit 128 comprise a network (e.g., a wireline network, wireless network, or some combination thereof) through which the tag reader and inventory control system 102 may be interfaced.

Figure 6:
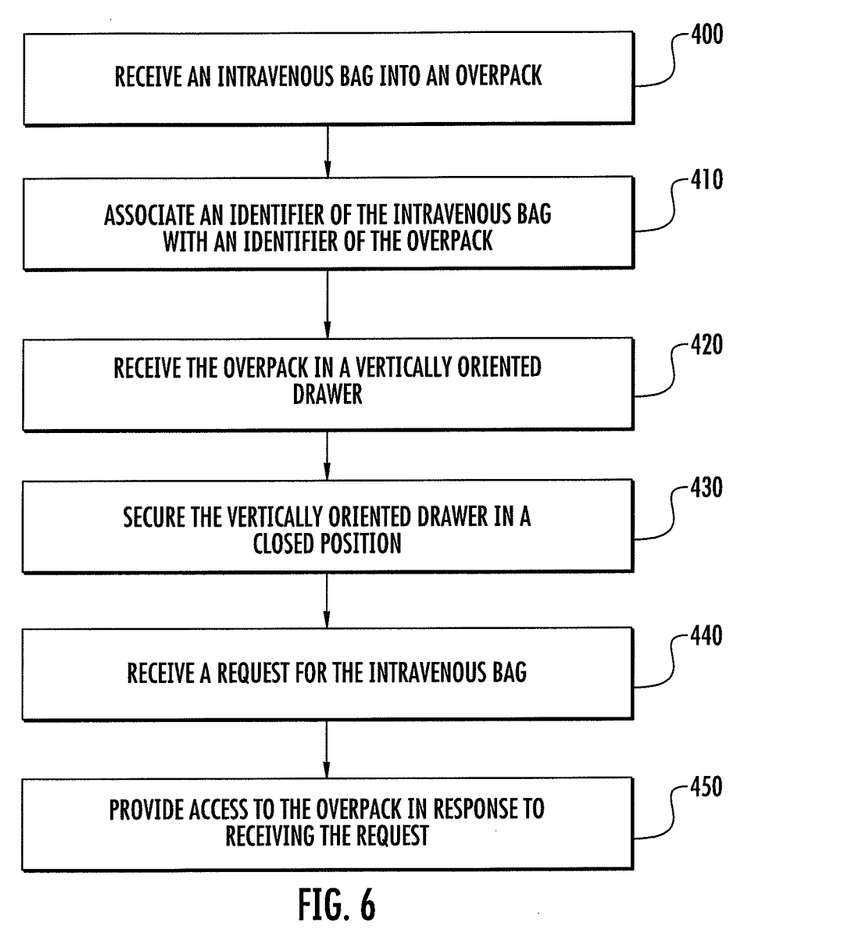
FIG. 6 is a flowchart of a method for controlling access to articles including intravenous bags according to an example embodiment of the present invention.

FIG. 6 illustrates a flowchart according to an example method for controlling access to intravenous bags according to some example embodiments. In this regard, FIG. 6 illustrates a method that may be at least partially performed by an inventory control system 102. The operations illustrated in and described with respect to FIG. 6 may, for example, be performed by, with the assistance of, and/or under the control of one or more of the processor 120, memory 122, communication interface 124, user interface 126, or detection unit 128. Operation 400 may include receiving an intravenous bag into an overpack. An identifier of the overpack may be associated with an identifier of the intravenous bag at 410. The association may be performed, for example, by scanning or reading a barcode, RFID tag, or other identifying indicia from each of the intravenous bag and the overpack. The association may be stored, for example, within a memory of the inventory control system. The overpack containing the intravenous bag may be received within a vertically oriented drawer at 420. The drawer may be closed and secured at 430. A request may be received by the inventory control system for the intravenous bag at 440. The request may be from an authorized medical person and received via user interface. The identity of the authorized medical person may be confirmed prior to performing operation 450 of providing access to the overpack in response to receiving the request.

The flowchart of FIG. 6 illustrates a system, method, and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a server, desktop computer, laptop computer, mobile computer, or other computing device (e.g., inventory control system 102) and executed by a processor (e.g., the processor 120) in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowcharts, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A system for controlling access to intravenous bags, the system comprising:
a cabinet comprising a vertically oriented drawer configured to be movable between an open position and a closed position relative to the cabinet, wherein the contents of the vertically oriented drawer are configured to be accessible from two opposing sides of the vertically oriented drawer when the drawer is in the open position; and
a plurality of overpacks configured to be received within the vertically oriented drawer of the cabinet,
wherein each of the plurality of overpacks is configured to receive therein a single intravenous bag;
wherein each of the plurality of overpacks includes a retention feature, wherein the retention feature of each overpack is configured to be received by a complementary retention feature in the vertically oriented drawer, wherein each overpack comprises a sensor configured to sense the presence of an intravenous bag within the overpack, and the system is configured to detect that the contents of an overpack of the plurality of overpacks has been removed.

2. The system of claim 1, wherein each overpack contained within the vertically oriented drawer is accessible from a first side of the drawer and an opposing second side of the drawer, wherein each of the plurality of overpacks is configured to be opened from both the first side of the drawer and the second side of the drawer.

3. The system of claim 1, wherein the retention feature of each overpack comprises a hook, and wherein the retention feature of the drawer comprises a rod.

4. The system of claim 1, wherein the vertically oriented drawer is individually lockable.

5. The system of claim 4, further comprising a visual indicator for the drawer to indicate if the drawer is unlocked.

6. The system of claim 1, wherein the system is configured to receive a signal from the sensor to determine if the corresponding overpack contains an intravenous bag.

7. The system of claim 1, wherein each of the plurality of overpacks comprises a unique identifier, and wherein an intravenous bag received within a respective overpack is associated with the unique identifier.

8. A method for controlling access to intravenous bags, the method comprising:
   receiving an intravenous bag into an overpack comprising a sensor configured to detect the presence of the intravenous bag within the overpack;
   associating an identifier of the intravenous bag with an identifier of the overpack;
   receiving the overpack in a vertically oriented drawer;
   securing the vertically oriented drawer in a closed position;
   receiving a request for the intravenous bag;
   providing for access to the overpack in response to receiving the request for the intravenous bag; and
   receiving an indication from the sensor that the intravenous bag within the overpack has been removed.

9. The method of claim 8, wherein providing for access to the overpack comprises causing the vertically oriented drawer containing the overpack to be unlocked.

10. The method of claim 9, wherein receiving a request for the intravenous bag comprises receiving a request for the intravenous bag and verifying the request is from an authorized medical person.

11. The method of claim 8, further comprising storing in a memory the identity and the location of the intravenous bag within the vertically oriented drawer.

12. The method of claim 11, further comprising providing for an indication of the location of the intravenous bag in response to receiving a request for the intravenous bag.

13. The method of claim 12, wherein providing for an indication of the location of the intravenous bag comprises providing a visual indicator of the vertically oriented drawer in which the intravenous bag is located.

14. The method of claim 8, further comprising receiving an indication that the contents of the overpack have been accessed.

15. The method of claim 14, further comprising updating an inventory of the vertically oriented drawer in response to receiving an indication that the contents of the overpack have been accessed.

16. A system for controlling access to intravenous bags, the system comprising:
   one or more vertically oriented drawers;
   a plurality of overpacks received within the one or more vertically oriented drawers, wherein each of the plurality of overpacks is configured to receive an intravenous bag, wherein each of the plurality of overpacks includes an identification, wherein each overpack comprises a sensor configured to sense the presence of an intravenous bag within the overpack;
   an inventory management system configured to receive an indication of the identification of an overpack of the plurality of overpacks and an identification of the intravenous bag received therein;
   wherein the inventory management system is further configured to receive an indication of access to an overpack of the plurality of overpacks and to update an inventory of the system in response to receiving the indication, and wherein the inventory management system is configured to receive an indication from a sensor that a respective intravenous bag has been removed from the respective overpack.

17. The system of claim 16, wherein the inventory management system is further configured to receive a request for an intravenous bag, and wherein the inventory management system is configured to provide access to an overpack of the plurality of overpacks containing the requested intravenous bag.

18. The system of claim 17, wherein the inventory management system is further configured to provide a visual indicator of a location of the overpack containing the requested intravenous bag in response to receiving the request for the intravenous bag.

* * * * *